United States Patent [19]

van Hooijdonk

[11] Patent Number: 5,028,485
[45] Date of Patent: Jul. 2, 1991

[54] PRESSURE SENSITIVE ADHESIVE COMPOSITION

[75] Inventor: Adrianus C. P. van Hooijdonk, Baarle-Hertog, Belgium

[73] Assignee: Avery International Corporation, Pasadena, Calif.

[21] Appl. No.: 246,981

[22] Filed: Sep. 20, 1988

[30] Foreign Application Priority Data

Sep. 24, 1987 [NL] Netherlands ............... 8702275

[51] Int. Cl.$^5$ .............................................. C08K 5/54
[52] U.S. Cl. .................................... 428/355; 428/356; 524/188; 604/365
[58] Field of Search ................ 524/188, 261, 262, 264, 524/265; 428/355, 356; 604/365, 366, 373, 389, 390; 427/208.4, 208.2; 525/221, 227

[56] References Cited

U.S. PATENT DOCUMENTS

| | | | |
|---|---|---|---|
| 3,644,245 | 2/1972 | Flanagan | 524/262 |
| 3,894,982 | 7/1975 | Polaski | 524/262 |
| 4,092,465 | 5/1978 | Uraneck et al. | 427/208.4 |
| 4,133,789 | 1/1979 | Lakshmanan | 524/188 |
| 4,147,831 | 4/1979 | Balinth | 428/356 |
| 4,212,756 | 7/1980 | Ashcraft et al. | 524/264 |
| 4,299,713 | 11/1981 | Maringer et al. | 264/261 |
| 4,323,557 | 4/1982 | Rosso et al. | 604/307 |
| 4,358,489 | 11/1982 | Green | 428/335 |
| 4,655,768 | 4/1987 | Marecki et al. | 604/307 |

*Primary Examiner*—Veronica P. Hoke
*Attorney, Agent, or Firm*—Christie, Parker & Hale

[57] ABSTRACT

The invention provides a pressure sensitive adhesive composition suitable for skin contact and comprising a polymer, copolymer or mixture of polymers and/or copolymers and optionally usual additives, and further comprising 1-20% by weight, based on the total amount of the composition, of at least one silane compound. Preferably the silane compound contains at least one amino functional group. Further the invention relates to a pressure sensitive adhesive tape and medical accessories provided with the above described adhesive composition.

8 Claims, No Drawings

PRESSURE SENSITIVE ADHESIVE COMPOSITION

This invention relates to a pressure sensitive adhesive composition among others suitable for skin contact, and comprising a polymer, copolymer or mixture of polymers and/or copolymers and optionally usual additives. Such an adhesive composition is suitable for medical use, for example for adhesion to the skin of operation drapes, electrodes, colostomy bags, incision foils, etc. The adhesive composition according to the invention may furthermore be used for example to label packed foodstuffs or for adhesion of plates of insulation material to each other or to a substrate.

This invention particularly relates to an adhesive composition which applied to a backing material, excellently adheres to optionally wet hydrophilic substrates and/or skin, and also adheres well when immersed in water. This invention relates in particular also to an adhesive composition which applied on labels, adheres excellently on optionally wet foil in which for example foodstuffs are packed or is also suitable as an adhesive composition for insulation material.

With operations hydrophilic non woven operation drapes are often used, which cover the patient with exception of the site of incision. Such operation drapes are often adhered to each other and round the site of incision to the skin with adhesive tape. During the operation body fluids and water will pass over the adhesive tape and are absorbed by the hydrophilic operation drapes, so that the floor around the operating table remains clean. These fluids will, however, also penetrate between the drape and the adhesive tape. By using conventional adhesive tape the adhesion of the adhesive composition will be totally lost. By using incision foils this problem also occurs. These foils of flexible plastic with an adhesive layer are adhered to the skin after sterilisation of the site of incision. By using conventional adhesive compositions one must wait with applying the foil until the sterilisation liquid is evaporated.

From U.S. Pat. No. 4,147,831 a pressure sensitive adhesive is known with a good adhesion, even in wet circumstances. This adhesive composition comprises an elastomeric mixture of natural rubber and polyisobutylene, a liquid plasticizer and a solid tackifier component. This adhesive is suitable as a component of adhesive tape for adhesion to the skin. The adhesion is retained when immersed in water. When, however, such an adhesive tape is applied to a hydrophilic non woven, and then is moistened, the adhesion will be lost.

U.S. Pat. No. 4,358,489 discloses a pressure sensitive adhesive laminate comprising a specific combination of carrier and adhesive, the adhesive comprising 0.5 to 20 parts of at least one oxidation stabilizer and at least one silane adhesion promoter. From example 2 it appears that a very small amount of silane compound is considered. In Compositions B and C γ-mercaptopropyltrimethoxy silane is included in an amount of less than 1% by weight. The adhesive used in this patent specification shows a high shear performance at elevated temperature. The object of the present invention is to provide a wetstick adhesive having much lower shear properties.

Besides adhesive compositions, based on elastomeric rubbers different other types of adhesive compositions have been developed for medical use, for example based on acrylate polymers or polyolefinic polymers. All adhesive compositions known have the above mentioned objection that they loose their adhesion when applied to hydrophilic non woven materials and then moistened.

Therefore, it is an object of the present invention to provide a pressure sensitive adhesive composition which is able to withstand water and body fluids when it is applied with an adhesive tape to a hydrophilic non woven substrate such as an operation drape. Further, the adhesive composition according to the invention should have a good adhesion when applied directly to wet skin or other wet substrates, for example foodstuffs packed in foil. Further, the adhesive composition according to the invention should meet the usual requirements, such as quick stick, adhesion over extended periods, correct cohesive and adhesive strength, no toxicity, etc.

It has now been found that adhesive compositions containing a certain amount of one or more silane compounds, have the above mentioned properties.

The present invention therefore relates to the adhesive composition mentioned in the preamble, characterized in that it comprises 1-20% by weight, based on the total amount of said composition, of at least one silane compound.

According to the invention a preferred pressure sensitive adhesive composition consists of:
a) 20-65% by weight, in particular 25-50% by weight of at least one synthetic or natural rubber,
b) 20-80% by weight, in particular 30-65% by weight of at least one liquid or solid tackifier,
c) 0-30% by weight, in particular 15-25% by weight of at least one liquid plasticizer,
d) 1-20% by weight, in particular 2-10% by weight of at least one silane compound,
e) 0-4% by weight of at least one anti-oxidant and optionally further usual additives.

Examples of silane compounds which may be included in the adhesive composition of the present invention are vinyltrimethoxy silane, γ-methacryloxypropyl trimethoxy silane, γ-glycidoxypropyl-trimethoxy silane, vinylacetoxy silane, mono-, di- and tri chloro functional silanes, methyl tri methoxy silane, vinyl tri ethoxy silane, vinyl tris (2-methoxy ethoxy)silane, gamma-methacryloxypropyl-tris-(2 methoxy ethoxy) silane, gamma-(3,4-epoxycyclohexyl)ethyl trimethoxy silane, mercapto functional silanes, gamma ureidopropyltriethoxy silane, N-2(vinylbenzylamino)ethyl-3-amino propyl tri-methoxy silane and tetra methoxy silane.

It has been found that silane compounds having at least one amino functional group give the best results. An example of such a compound is γ-aminopropyl trimethoxy silane, $NH_2-CH_2-CH_2-CH_2-Si(-O-CH_3)_3$.

Furthermore, it has been found that the best properties are obtained in particular on hydropholic non wovens according as the number of amino functional groups in the silane compound increases. An example of such a silane compound having more than one amino functional group is N—(2-aminoethyl)—N— (3-trimethoxy silyl propyl) —1, 2-ethane diamine $NH_2-CH_2-CH_2-NH-CH_2-CH_2-NH-CH_2-CH_2-CH_2-Si(OCH_3)_3$. The above mentioned silane compounds are commercially available.

With the term "synthetic or natural rubber" used in the above mentioned preferred composition elastomers are meant such as for example natural or synthetic cis-1,4-polyisoprene, butyl rubber, polyisobutylene, styrene-butadiene block copolymers, styrene-isoprene block copolymers, styrene-butadiene-styrene block copolymers, styrene-isoprene-styrene-block copolymers, styrene-ethylene-butylene-styrene block copolymers, acrylonitrile-butadiene copolymers and ethylene-propylene copolymers. The above mentioned polymers are known rubbers suitable in adhesive compositions. Specific properties such as the molecular weight are known for experts. Thus styrene-butadiene-styrene-block copolymers for use in the adhesive composition of the invention preferably have a molecular weight of 80,000–180,000 and a ratio styrene: butadiene of 15:85 to 45:55. Preferably a mixture of such elastomeric rubbers is used.

With the term "liquid or solid tackifier" resins are meant such as for example hydrocarbon resins, pentaerythritol esters, polyterpene resins, phenolic resins and glycerol esters, preferably with a softening point above 100° C. Preferably a mixture of tackifiers is used in order to obtain the correct cohesion and adhesion strength. Thus the use of only liquid tackifier gives a bad cohesion, adhesive rests remaining on the substrate after removal of adhesive tape coated with said adhesive composition.

The liquid plasticizer in the preferred composition according to the invention is important for the softening and the reduction of the viscosity of the adhesive composition. Examples of suitable plasticizers are high molecular weight liquid polybutenes, mineral oils and white mineral oils. When more than 30% by weight of liquid plasticizer is present in the adhesive composition, the viscosity of the adhesive gets too low and may bleed out.

An amount of plasticizer between 15 and 25% by weight gives the best results. Due to the relative high amount of plasticizer the viscosity of the adhesive composition is rather low which allows the adhesive to get a good grip on the fibers of the non woven and retain its adhesion when fluids penetrate between adhesive tape and non woven.

If desired, the adhesive composition of the present invention may contain anti-oxidants, pigments, fillers and other usual additives. Anti-oxidants are generally used in an amount of 0–4% by weight. Suitable anti-oxidants are for example mixtures of phenolic anti-oxidants and dilaurylesters of $\beta, \beta'$-thiodipropionic acid. Such mixtures give a synergetic effect regarding the inhibition of oxidation reactions. Pigments such as titanedioxide or talc are usually included in an amount of no more than 5% by weight. Suitable fillers include for example hygroscopic materials such as cellulose powders, gelatin, carboxymethyl cellulose and the like. The adhesive composition of the invention contains fillers up to 10% by weight in order to retain good adhesive properties.

In addition to the above mentioned polymeric components the adhesive composition of the present invention can also include a polymeric base of the polyacrylic or silicone type, which include styrene, vinyl pyrrolidone, vinyl acetate, methacrylic and/or acrylic acid as possible monomers.

This invention furthermore relates to a pressure sensitive adhesive tape which is among others suitable for adhesion to optionally wet hydrophilic substrates and/or skin, and consists of a flexible backing material onto which a pressure sensitive adhesive composition of the present invention is coated. Suitable flexible backing materials are for example polymeric films, paper and other usual materials. It is to be understood that the invention also includes backing materials onto which at both sides an adhesive composition is coated and so called "transfer tapes", consisting of an adhesive composition layer between two temporary backing materials. The adhesive composition can be coated by any known methods.

This invention furthermore relates to medical accessories provided with an adhesive composition and/or adhesive tape according to the invention for applying to the skin. Such medical accessories are for example electrodes, colostomy bags, incision foils and bandages or operation drapes with an adhesive tape. Some of these accessories such as incision foils have to be sterilized. Sterilization can occur by various known methods. In the examples the properties of the adhesive compositions of the present invention are examined with the following tests.

A) 180° peel adhesion on wet hydrophilic viscose based non woven

Samples are conditioned for 24 hours at 23° C.±2° C. at 50% relative humidity, prior to start testing. The standard test substrate (viscose based hydrophilic non woven operation drape) is applied to a stainless steel panel by means of a double coated tape. Test specimens of a hydrophobic viscose polyester based non woven coated with the pressure sensitive adhesive composition of the invention with a coating weight of 60 g/m² are cut out with dimension 2,5×15 cm. The test specimens are laminated upon the hydrophilic non woven once in each direction with a 0,5 kg roller. After 30 min. an excess (minimal 2 ml per specimen) of destilled water is added over the whole length at one side of the adhesive tape, and the water is allowed to penetrate underneath the adhesive tape to the other side. After 5 min. dwell the adhesive tape is peeled off from the non woven under an angle of 180° with a tensile tester at a speed of 300 mm/min. The average peel off value is recorded in N/m.

B) Jogging-showering test (accelerated sweat resistancy test)

Samples are conditoned for 24 hours at 23°±2° C. at 50% relative humidity, prior to start testing. The inside of the front arm of a test subject is washed with soap and water and then scoured with alcohol. The alcohol is allowed to evaporate. Test specimens of a hydrophobic viscose polyester based non woven, coated with the pressure sensitive adhesive composition of the invention with a coating weight of 60 g/m² are cut with dimension 2,5×5 cm. The test specimens are laminated upon the cleaned inside of the front arm manually. After 20 min the test subject must excercise the body for about 20–30 min so that the body of the test subject perspires. Then the test subject must take a shower with hand warm water, i.e. about 40° C. Then the adhesive tape is peeled off manually to check the adhesion left. The observed adhesion strength is judged as "poor, good or excellent". This judgement is subjective and varies upon the person performing this test. However, the test gives an indication about the resistance against perspiration and water of the adhesive composition of the invention on the skin.

C) Skinfriendliness

The inside of the front arm of a test subject is washed with soap and water and then scoured with alcohol. The alcohol is allowed to evaporate. Test specimens of a hydrophobic viscose polyester based non woven coated with the pressure sensitive adhesive composition of the invention with a coating weight of 60 g/m are cut with dimension 2,5×15 cm. The test specimens are laminated upon the cleaned inside of the front are manually. After 4 hours the adhesive tape is removed manually. The skin is controlled for irritation after 30 min.

Hereafter, the invention is illustrated by the following examples. It is understood, however, that these examples are not meant to restrict the invention, but only should indicate the scope of the invention.

EXAMPLE I

A number of adhesive compositions are prepared and the properties are examined with the above mentioned tests. The results are mentioned in table A.

TABLE A

| | % by weight | | | | | | | |
|---|---|---|---|---|---|---|---|---|
| Rubbers | 32.8 | 32.4 | 32.1 | 31.8 | 31.5 | 31.2 | 30.9 | 30.3 |
| Solid tackifiers | 46 | 45.5 | 45.1 | 44.6 | 44.2 | 43.8 | 43.4 | 42.6 |
| Liquid plasticizer | 19.6 | 19.4 | 19.2 | 19 | 18.8 | 18.7 | 18.5 | 18.2 |
| Silane compound | 0 | 1 | 2 | 2.9 | 3.8 | 4.8 | 5.7 | 7.4 |
| Anti-oxydants | 1.7 | 1.7 | 1.7 | 1.7 | 1.6 | 1.6 | 1.6 | 1.6 |
| 180° peel adhesion (N/m) | 20 | 35 | 65 | 96 | 112 | 132 | 124 | 116 |
| Jogging-showering test | poor | poor | good | good | good | exc. | exc. | exc. |
| Skinfriendliness | good | good | good | good | good | good to slight irr. | good to slight irr. | good slig irr. |

The rubbers used in this and the following examples are mixtures of SBS and SIS rubbers. The solid tackifiers used for mixtures of polyterpene resin, mixed olefin resin and pentaerythritol ester. The liquid plasticizer used is mineral oil. In this example N-(2-aminoethyl)-N-(3-trimethoxy silyl propyl)-1,2-ethane diamine is used as a silane compound. The anti-oxidants used are mixtures of phenolic and thiopropionic acid anti-oxidants.

In the series of adhesive compositions of this example only the ratio (amino-silane/rest of formulation) is changed. The ratios between rubbers, resins, plasticizers and anti-oxidants are not changed. It appears from the results that increasing aminosilane contents increase the adhesion on hydrophilic non woven in which water has penetrated. In addition, also skin adhesion increases. When about 5% by weight or more aminosilane compound is present in the adhesive composition, it may slightly irritate the skin of some test persons; this is seen as local barely perceptible redness, which may occur immediately after removal, but vanishes very quickly. This irritation is not caused by toxic components, or chemical reactions but by increasing of adhesion strength of the formulation.

When the adhesive of the present invention is used for medical accessories, the specimen needs to be sterilized. Either ethylene oxide (EtO) sterilization, either gamma ray sterilization are suitable methods. The effect of EtO sterilization on the result of the 180° peel adhesion test is seen as an about 30% decrease just after sterilization, leveling back to a decrease of about 15% after 1 month. The EtO gas is then completely migrated out of the specimen. The effect of gamma ray sterilization on the result of the 180° peel adhesion test is seen as a 10–15% decrease just after sterilization. In ageing, this adhesion remains at this decreased level.

EXAMPLE II

A number of adhesive compositions are prepared with the same components as mentioned in Example I, except that silane compounds having a different number of amino functional groups are used. The properties are examined again with the tests mentioned above. The results are mentioned in table B.

TABLE B

| | % by weight | | |
|---|---|---|---|
| Rubbers | 31.5 | 31.5 | 31.5 |
| Solid tackifiers | 44.2 | 44.2 | 44.2 |
| Liquid plasticizer | 18.8 | 18.8 | 18.8 |
| Silane compound with 1 NH | 3.8 | — | — |
| Silane compound with 2 NH | — | 3.8 | — |
| Silane compound with 3 NH | — | — | 3.8 |
| Anti-oxydants | 1.6 | 1.6 | 1.6 |
| 180° peel adhesion (N/m) | 48 | 96 | 112 |
| Jogging-showering test | poor | good | good |
| Skinfriendliness | good | good | good |

The silane compounds having 1, 2 and 3 amino functional groups are γ-aminopropyl trimethoxysilane, N-β-(aminoethyl)-γ-aminopropyl trimethoxy silane and N-(2-aminoethyl)-N-(3-trimethoxy silyl propyl)-1,2-ethane diamine respectively. It appears from table B that the adhesive composition according to the invention has increasing resistance against water, when silane compounds having increasing numbers of amino functional groups are added.

EXAMPLE III

A number of adhesive compositions are prepared with the same components as mentioned in Example I. In these compositions only the ratio (liquid plasticizer/rest of the composition) is changed. The ratios between rubbers, resins, silane compound and anti-oxidants are constant. The properties are again examined with the tests mentioned above. The results are mentioned in table C.

TABLE C

| | % by weight | | | |
|---|---|---|---|---|
| Rubbers | 31.5 | 32.7 | 33.7 | 34.7 |
| Solid tackifiers | 44.2 | 45.9 | 47.3 | 48.8 |
| Liquid plasticizer | 18.8 | 15.7 | 13.1 | 10.4 |
| Silane compound | 3.8 | 4 | 4.1 | 4.2 |
| Anti-oxydants | 1.6 | 1.7 | 1.8 | 1.8 |
| 180° peel adhesion (N/m) | 112 | 92 | 80 | 72 |
| Jogging-showering test | good | good | good | good |
| Skinfriendliness | good | good | good | good |

It appears from table C that decreasing amounts of liquid plasticizer decrease the adhesion strength on hydrophilic non woven in which water has penetrated.

I claim:

1. In combination a medical accessory or tape provided with pressure sensitive adhesive composition, which pressure sensitive adhesive retains adhesion to hydrophilic surfaces and skin under wet conditions and which pressure sensitive adhesive composition comprises:
- a) 20–65% by weight of at least one synthetic elastomer or natural rubber,
- b) 20–80% by weight of at least one liquid or solid tackifier,
- c) 7.5–30% by weight of at least one liquid plasticizer,
- d) 1–20% by weight of at least one silane compound containing at least one amino functional group,
- e) 0–4% by weight of at least one anti-oxidant.

2. The combination as claimed in claim 1, in which the silane compound is a silane having at least two amino functional groups.

3. A combination as claimed in claim 1 in which the adhesive comprises:
- a) 25–50% by weight of at least one synthetic elastomer or natural rubber,
- b) 30–65% by weight of at least one liquid or solid tackifier,
- c) 15–25% by weight of at least one liquid plasticizer,
- d) 2–10% by weight of at least one silane compound, having at least one amino functional group,
- e) 0–4% by weight of at least one anti-oxidant.

4. The combination claimed in claim 3 in which the silane compound is a silane having at least two amino functional groups.

5. The combination as claimed in claim 3 in which the silane compound is N-(2-aminoethyl)-N-(3-trimethoxy silyl propyl)-1, 2-ethane diamine.

6. The combination as claimed in claim 1 in which the combination is sterilized.

7. The combination as claimed in claim 1 in which the silane compound is N-(2-aminoethyl)-N-(3-trimethoxy silyl propyl)-1, 2-ethane diamine.

8. The combination as claimed in claim 7 in which the combination is sterilized.

* * * * *

UNITED STATES PATENT AND TRADEMARK OFFICE
CERTIFICATE OF CORRECTION

PATENT NO. : 5,028,485
DATED : July 2, 1991
INVENTOR(S) : Adrianus C.P. van Hooijdonk It is certified that error appears in the above-identified patent and that said Letters Patent is hereby corrected as shown below:

Column 1, line 8, after "optionally" and before "usual" insert -- further --.
Column 1, line 25, change "non woven" to -- nonwoven --.
Column 1, line 50, change "non woven" to -- nonwoven --.
Column 1, line 65, after "rubbers" insert a comma.

Column 2, lines 2,7,8, change "non woven" to -- nonwoven -- (both occurrences).
Column 2, lines 55,56, change "hydropholic non woven" to -- hydrophilic nonwoven --.

Column 3, line 21, after "cohesion," delete "adhesive rests remaining" and insert therefor -- and the adhesive remaining rests --.
Column 3, lines 37,39, change "non woven" to -- nonwoven -- (both occurrences).

Column 4, line 19, change "non woven" to -- nonwoven --.
Column 4, lines 22,23,25, change "non woven" to -- nonwoven -- (both occurrences).
Column 4, lines 29,35, change "non woven" to -- nonwoven -- (both occurrences).
Column 4, line 31, change "destilled" to -- distilled --.
Column 4, line 47, change "non woven" to -- nonwoven --.
Column 4, line 50, change "2,5X5 cm" to -- 2,5X15 cm --.
Column 4, line 52, change "excercise" to -- exercise --.
Column 4, line 54, after "with" delete "hand".
Column 4, line 68, change "non woven" to -- nonwoven --.

UNITED STATES PATENT AND TRADEMARK OFFICE
CERTIFICATE OF CORRECTION

PATENT NO. : 5,028,485
DATED : July 2, 1991
INVENTOR(S) : Adrianus C.P. van Hooijdonk It is certified that error appears in the above-identified patent and that said Letters Patent is hereby corrected as shown below:

```
Column 5, line 32, after "used" delete "for" and insert
                   therefor -- are --.
Column 5, line 43, change "non woven" to -- nonwoven --.
Column 5, line 58, change "as an about 30%" to -- as about a
                   30% --.

Column 6, line 64, change "non woven" to -- nonwoven --.
```

Signed and Sealed this

Twenty-fifth Day of May, 1993

Attest:

MICHAEL K. KIRK

*Attesting Officer*    *Acting Commissioner of Patents and Trademarks*